United States Patent [19]
Arru et al.

[11] Patent Number: 5,423,886
[45] Date of Patent: Jun. 13, 1995

[54] CYCLICALLY DEFORMABLE HAEMOCOMPATIBLE AND BIOCOMPATIBLE DEVICES COATED WITH BIOCOMPATIBLE CARBONACEOUS MATERIAL

[75] Inventors: Pietro Arru, Turin; Stefano Rinaldi, Parma; Marco Santi; Franco Vallana, both of Turin, all of Italy

[73] Assignee: Sorin Biomedica S.p.A., Italy

[21] Appl. No.: 110,419

[22] Filed: Aug. 23, 1993

Related U.S. Application Data

[63] Continuation of Ser. No. 985,555, Dec. 3, 1992, abandoned, which is a continuation of Ser. No. 192,389, May 10, 1988, abandoned.

[30] Foreign Application Priority Data

May 11, 1987 [IT] Italy .................................. 67402/87

[51] Int. Cl.⁶ ............................................. A61F 2/06
[52] U.S. Cl. .......................................... 623/1; 623/66; 623/2; 623/3; 604/266
[58] Field of Search .................. 623/1, 2, 3, 66, 901; 606/191; 604/266; 427/2

[56] References Cited

U.S. PATENT DOCUMENTS 3,526,005  9/1970  Bokros et al. ............................. 623/1
3,952,334  4/1976  Bokros et al. ............................. 623/1

FOREIGN PATENT DOCUMENTS 3116040  11/1982  Germany .
2112472  7/1983  United Kingdom .

Primary Examiner—Paul Prebilic
Attorney, Agent, or Firm—Rogers & Wells

[57] ABSTRACT

There are disclosed devices for conditioning a blood flow which include at least one element with portions which are exposed to the blood and are deformable cyclically at a frequency comparable to the frequency of the heartbeat, in which the cyclically deformable portions have a continuous coating of biocompatible carbonaceous material comprised of carbon crystals having a density of greater than 2.1 grams per cubic centimeter applied by sputtering directly on and completely covering at least those portions of the device which are exposed to the blood.

6 Claims, 1 Drawing Sheet

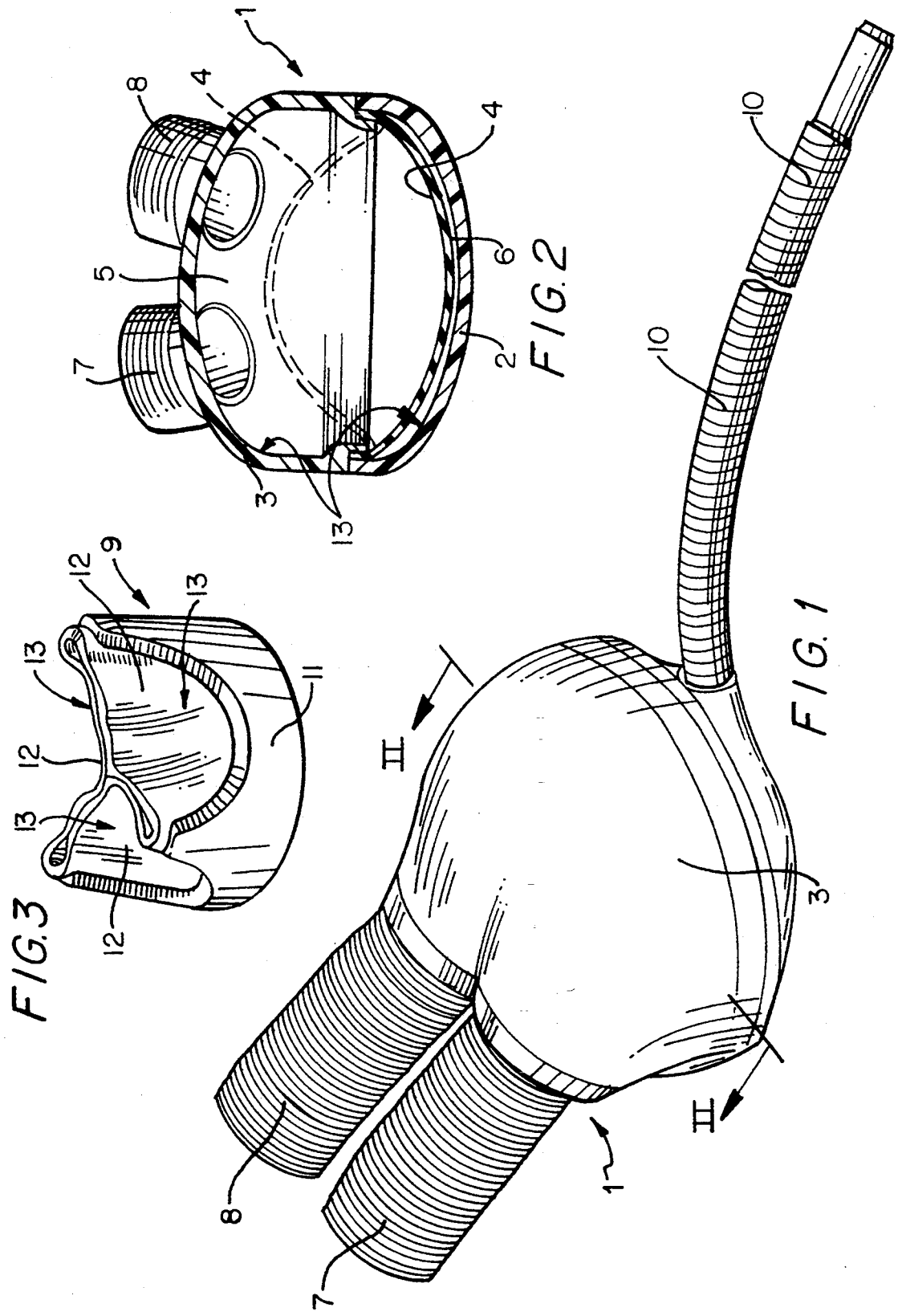

CYCLICALLY DEFORMABLE HAEMOCOMPATIBLE AND BIOCOMPATIBLE DEVICES COATED WITH BIOCOMPATIBLE CARBONACEOUS MATERIAL

This is a continuation of application Ser. No. 07/985,555, filed Dec. 3, 1992, (now abandoned) which is a continuation of application Ser. No. 07/192,389, filed May 10, 1988 (now abandoned).

DESCRIPTION

The present invention relates to devices for conditioning a blood flow and concerns, in particular, devices which include at least one element having portions which are exposed to the blood and are deformable cyclically at a frequency comparable to the frequency of the heartbeat.

Devices of this type may include, for example, a blood chamber with at least one deformable wall portion, the deformation being usable to pump the blood.

This is the case, for example, in so-called blood pumps for ventricular-assistance systems which are fitted to patients affected by very serious cardiac insufficiency whilst awaiting the recovery of the functioning of the natural or implanted biological heart, or whilst awaiting a transplant, or, indeed, in pumps used for establishing circulation outside the body during open-heart surgery. Structurally-similar devices are constituted by so-called artificial ventricles or artificial hearts which can be implanted in the body of a patient to replace or assist a diseased heart muscle.

The most recent results of research in the field of devices for assisting or replacing parts or functions of the cardiovascular system have demonstrated the advantages and limitations of the use of polymeric materials used up till now in the production of these devices. This relates, in particular, to polymeric parts made from sheets, films or tubes of polymeric substances with continuous or microporous structures, and smooth or rough surfaces.

The use of this type of material has also been considered for the production of cyclically-deformable parts exposed to the blood in other blood-flow conditioning devices, for example for the production of the valve leaflets of heart-valve prostheses (or, in short valves). In the latter case, one is concerned with an extension of the use of polymeric materials: according to solutions which can now be considered conventional, materials of this type are used in the production of the stent of the valve or (in the form of threads variously woven or interlaced) in the production of the suture ring thereof.

The use of polymeric materials for the production of valve leaflets opens up a completely new field of use since it involves the use of the polymeric material not only for producing elements (such as the stent or the suture ring) which must have a certain degree of flexibility in order to adapt to the implant situation, but also for producing elements (such as the leaflets) which are to be deformed cyclically at a frequency substantially equal to the frequency of the heartbeat.

This aspect thus has a substantial affinity with the problems found in use of the blood-pumping devices described above.

The polymers most commonly used in the cardiovascular field are polyurethanes and polytetrafluorethylene (PTFE) with a lesser use of other synthetic polymers such as polyesters or silicone polymers.

A characteristic common to the materials concerned is that of being produced in a macroscopically continuous form, whilst the microstructure of the materials in question may be solid or microporous, this being affected by the synthesising of production technique.

The main advantages of these materials in use in the cardiovascular field are their good mechanical properties, resilience and flexibility associated with their ability to contain the blood without allowing it to seep through the material appreciably. Even in the case of microporous materials, in fact, the dimensions of the pores are such as to allow a moderate penetration of biological cells, but not significant blood flow.

Other advantageous characteristics of these materials are in their good chemical inertness and stability, even in a biological environment.

These characteristics, are not, however, accompanied by a wholly satisfactory degree of biocompatibility and haemocompatibility.

This incomplete compatibility gives rise to some phenomena which limit significantly the possibilities of use of these materials in the production of blood-flow conditioning devices.

A first harmful effect is the formation of thrombi and/or clotting on contact with the blood. These thrombi may become detached, causing embolisms, or grow until they reduce the effectiveness of the device, giving rise to stiffening, if not quite to obstruction.

Another harmful effect is the formation, on contact with the blood, of a neo-intima or pannus which may increase in thickness excessively until it compromises the functioning of the device.

Other problems are due to the tendency to the formation of centres of infection which are resistant to antibiotic treatment and to interaction with the surrounding tissues, which can give rise to adhesion and/or the formation of inflammation.

The object of the present invention is to provide devices for conditioning a blood flow, of the type specified above, which do not give rise to the problems described.

According to the present invention this object is achieved by a device for conditioning a blood flow of the type specified above, characterised in that the said one cyclically-deformable element is coated with biocompatible carbonaceous material, at least on part of the portions thereof exposed to the blood.

A coating of this type, which may even be applied to a continuous polymeric material with a low melting point with the use of the methods described in European patent applications Nos. 0 102 328 and 0 224 080, in the name of the same Applicant, confers optimal characteristics of haemocompatibility and biocompatibility on the surface of the device, considerably improving the properties of the device itself and at the same time retaining the positive characteristics deriving from the polymer used to produce the structure.

Both the previous European patent applications cited above describe the possibility of depositing a layer of biocompatible carbonaceous material on a polymeric material having a certain degree of flexibility, such as that required, for example, for the stent of heart valve prosthesis.

The present invention is based on the observation that, in a completely surprising and unexpected manner, a film of biocompatible carbonaceous material may be deposited on an element deformable at a frequency comparable to the frequency of the heartbeat (such as a pulsating wall of the blood chamber of a pump for ventricular-assistance systems or a valve leaflet of a heart prosthesis) without resulting in the detachment or cracking of the layer of biocompatible material.

BRIEF DESCRIPTION OF THE DRAWINGS

The invention will now be described purely by way of non-limiting example with reference to the appended drawings, in which:

FIG. 1 shows a first device for conditioning a blood flow constituted by a so-called artificial ventricle produced according to the invention, FIG. 2 is a section taken on the line II—II of FIG. 1, and FIG. 3 is a perspective view of a heart valve prosthesis also produced according to the invention.

The device illustrated in FIGS. 1 and 2, generally indicated 1, comprises a casing of substantially-rigid or moderately-flexible plastics material, usually constituted by two shells 2 and 3 between which a flexible diaphragm 4, also made, of a continuous polymeric material, such as a thin sheet of polyurethane, is interposed. The device can also contain a cyclically-deformable element made of materials such as polyurethanes, polytetrafluoroethylene, polyesters, and silicone polymers.

The diaphragm 4 divides the space within the device 1 into two chambers indicated 5 and 6 respectively in the sectioned view of FIG. 2.

The chamber 5 constitutes the so-called blood chamber of the device 1 which is intended for use in generating a pulsed blood flow to replace or assist a natural ventricle or heart muscle which is diseased or undergoing a surgical operation.

For this purpose a blood supply duct 7, usually connected to a heart atrium or a device which simulates its function, and a blood delivery duct 8, intended for connection to or to replace the patient's aorta, are connected to two orifices provided in the blood chamber 5.

Both the ducts 7 and 8 may be constituted by artificial ducts, such as those usually referred to as "vascular grafts" or other artificial ducts such as cannulae.

The ducts 7 and 8 normally have respective associated valves which may have structures similar to that of the valve 9 illustrated in FIG. 3, which will be returned to below.

A further pumping duct 10 opens into the second chamber 6, or pumping chamber, of the device 1, and through this it is possible to supply a pulsed hydraulic or pneumatic flow into the chamber 6 whose function is to deform the diaphragm 4 rhythmically from the position shown in a continuous line in FIG. 2 (position corresponding to the maximum volume of the blood chamber 5) to the position shown schematically in broken outline in the same drawing (the position which corresponds to the maximum reduction in voluble of the blood chamber 5).

By means of the rhythmic deformation of the diaphragm 4 caused by the supply to the pumping chamber 6 governed by regulating action exerted alternatively by the valves associated with the ducts 7 and 8, the device 1 enables a pulsed flow of blood to be generated at the output of the duct 8, thus fulfilling a function completely analogous to that of the ventricles of a natural heart muscle.

The structure of the device 1 described above must be considered entirely known. It is, however, illustrative in character, numerous other solutions having been proposed which enable a completely similar function to be achieved by the cyclic compression of the blood chamber by means of a different type.

It has, in fact, been suggested, for example, to use devices which are operated electrically, electromagnetically, or even by the contraction of a suitably conditioned skeletal muscle of the patient instead of a thrusting action exerted pneumatically or hydraulically.

A fundamental characteristic of all the devices in question is the presence of at least one wall in the blood pumping chamber which is exposed to the blood and is cyclically deformed at a frequency comparable to the frequency of the heartbeat.

An essentially similar situation is found in valve prostheses such as the prosthesis or valve indicated 9 in FIG. 3. In addition to a stent 11 of substantially rigid or moderately flexible material (and possibly a suture ring not illustrated in the drawings), the valve 9 includes one or more valve leaflets 12 which are intended to deform cyclically at a frequency similar to the frequency of the heartbeat to allow the blood to flow freely through the prosthesis 9 in one direction and to stop the flow in the opposite direction as a result of the converging movement of the valve leaflets 12 to obstruct the central orifice of the stent 11.

Three valve leaflets 12 are usually provided in a configuration which reproduces essentially the configuration of physiological aortic valves. Models with one or two leaflets are also known, as is the possibility of using yet a different number.

The fundamental characteristic of the devices 1 and 9 produced in accordance with the invention is the fact that at least the elements thereof which are exposed to the blood and intended to be deformed cyclically at the heartbeat frequency (in the specific case, the diaphragm 4 and the valve leaflets 12) have a layer (film) 13 of biocompatible carbonaceous material which covers them completely or covers the most critical parts thereof.

In particular, as far as the diaphragm 4 is concerned, the coating is applied to the surface facing the blood chamber 5. It may, however, also be advantageous to apply the same coating to the internal wall of the casing 3 and to the surfaces of the blood ducts 7 and 8, as well as to the diaphragm 4.

In this way, all the parts of the device 1 which are intended to come into contact with the blood are coated with carbonaceous material and are completely haemocompatible and biocompatible.

Naturally, if the device 1 as a whole is intended to be implanted in a patient's body or, at least, if its outer surface is also to come into contact with biological masses, it may be advantageous to apply the coating 33 to the outer surface of the device as well.

This is also true—a fortiori—for the valve prosthesis 9, whose stent parts and any suture ring may be coated with biocompatible carbonaceous material as well as the valve leaflets 13 (on one or both the opposite faces thereof).

The best results are obtained with a film of biocompatible carbonaceous material having an intrinsically turbostratic structure with a density greater than or equal to approximately 2.1 $g/cm^2$ and a thickness of between about 0.1 and about 1 micron. The dimensions of the carbon crystals in such a film are less than about 100 Å.

It has been able to be shown that such a coating film is not subject to detachment and/or cracking even if applied to highly flexible elements such as the diaphragm 4 of the device 1 and the valve leaflets 12 of the valve 9, which are intended to be deformed cyclically at a frequency comparable to the frequency of the heartbeat, that is to say, at a frequency of from about 25 to about 200 beats/minute.

The film 13 may be deposited by various techniques known in the art. Particularly good results are obtained by the sputtering methods and equipment described in European patent applications Nos. 0 102 328 and 0 224 080 in the name of the same Applicant already quoted above.

To produce the required adhesion of the deposited carbon without adversely affecting the substrate, high voltages and low currents are used for the target 20.

It has been found that the relatively high voltages, e.g., at least about 500 volts and preferably about 1000 to 3000 volts, provide the energy needed to properly adhere the sputtered carbon to the substrate and suitable deposition rate, while low direct currents, e.g., about 0.05 to 0.3 amps., minimize infrared and ultraviolet radiation. On the other hand, low voltage levels adversely affect the adhesion of the carbon to the substrate without meaningfully changing the generation of infrared radiation and high currents produce infrared and ultraviolet radiation that can adversely affect the substrates.

We claim:

1. A device for conditioning a blood flow including at least one element with portions which are exposed to the blood, are completely haemocompatible and biocompatible and are deformable cyclically at a frequency of from about 25 to about 200 cycles/minute, wherein said portions which are exposed to blood have a continuous coating of biocompatible carbonaceous material comprised of carbon crystals having a size of less than approximately $10^{-8}$ meters and having a density of greater than 2.1 gm/cm$^3$ applied by sputtering directly on and completely covering at least the portions which are exposed to the blood, wherein said portions which are exposed to blood are comprised of a polymeric material selected from the group consisting of polyurethanes, polytetrafluorethylenes, polyesters and silicone polymers.

2. A device according to claim 1, wherein said coating is constituted by carbonaceous material with an intrinsically turbostratic structure.

3. A device according to claim 1, wherein said coating has a thickness substantially between 0.1 and 1 micron.

4. A device according to claim 1, comprising a blood chamber with at least one wall portion which is deformable cyclically to pump the blood, wherein said coating of biocompatible carbonaceous material is provided at least on part of this deformable portion of wall.

5. A device according to claim 1, wherein said coating of biocompatible carbonaceous material is provided on substantially the whole of the device.

6. A device for conditioning a blood flow including at least one element with portions that are exposed to the blood, are completely haemocompatible and biocompatible and are deformable cyclically at a frequency of from about 25 to about 200 cycles/minute, wherein said portions which are exposed to blood have a continuous coating of biocompatible carbonaceous material comprised of carbon crystals having a size of less than approximately $10^{-8}$ meters and having a density of greater than 2.1 gm/cm$^3$ applied by sputtering directly on and completely covering the portions which are exposed to the blood, and wherein the sputtering is performed under high voltage, low current conditions.

* * * * *